United States Patent [19]

Derenzo et al.

[11] Patent Number: 4,473,749

[45] Date of Patent: Sep. 25, 1984

[54] CLAMSHELL TOMOGRAPH

[75] Inventors: Stephen E. Derenzo, Pinole; Thomas F. Budinger, Berkeley, both of Calif.

[73] Assignee: The United States of America as represented by the United States Department of Energy, Washington, D.C.

[21] Appl. No.: 344,161

[22] Filed: Jan. 29, 1982

[51] Int. Cl.³ .............................................. G01T 1/20
[52] U.S. Cl. ................................................. 250/363 S
[58] Field of Search ....................... 250/363 S; 378/19

[56] References Cited

PUBLICATIONS

Phelps et al., "Application of Annihilation Coincidence Detection to Transaxial Reconstruction Tomography", J. Nucl. Med. 16, 1975, pp. 210-224.
Mullani et al., "Engineering Aspects of PETT V", IEEE Trans. Nucl. Sci., NS-26, No. 2, 2703-2706, 1979.
Ter-Pogossian et al., "A Multislice Positron Emission Computed Tomograph (PETT IV) Yielding Transverse and Longitudinal Images, Radiology, 128: 477-484, 1978.
Williams et al., "Design and Performance Characteristics of a Positron Emission Computed Axial Tomograph ... ECAT-II", IEEE Trans. Nucl. Sci., NS-26, No. 1, 619-627, 1979.
Eriksson et al., "A Computer Assisted Ring Detector Positron Camera System for Reconstruction Tomography of the Brain", IEEE Trans. Nucl. Sci., NS-25: No. 1, 624-637, 1978.
Brooks et al., "Sampling Requirements and Detector Motion for Positron Emission Tomography", IEEE Trans. Nucl. Sci., NS-26, No. 2, 2760-2763, 1979.
Tanaka et al., "Positology-The Search for Suitable Detector Arrangements for a Positron ECT with Continuous Rotation", IEEE Trans. Nucl. Sci., NS-26, No. 2, 2728-2731, 1979.
Nohara et al., "Positologica: A Positron ECT Device with a Continuously Rotating Detector Ring", IEEE Trans. Nucl. Sci., NS-27, No. 3, 1128-1136, 1980.
Cho et al., "A New Sampling Scheme for the Ring Positron Camera: Dichotomic Ring Sampling", IEEE Trans. Nucl. Sci., NS-28, No. 1, 94-98, 1981.
Derenzo et al., "High Resolution Computed Tomography of Positron Emitters", IEEE Trans. Nucl. Sci., NS-24, No. 1, 544-558, 1977.
Derenzo et al., "Design and Construction of the Donner 280-Crystal Positron Ring for Dynamic Transverse Section Emission Imaging", Proceedings of the IEEE Conference on Decision & Control, IEEE 77CH1269-OCS, vol. 1, 1977, 341-349.
Derenzo et al., "The Donner 280-Crystal High Resolution Positron Tomograph", IEEE Trans. Nucl. Sci., NS-26, No. 2, 2790-2793, 1979.
Huesman et al., "Data Acquisition, Reconstruction and Display for the Donner 280-Crystal Positron Tomograph", IEEE Trans. Nucl. Sci., NS-27, No. 1, 474-478, 1980.
Herman et al., "Reconstruction from Divergent Beams: A Comparison of Algorithms with and without Rebinning", Computers in Biology and Medicine, vol. 10, 131-139, 1980.

(List continued on next page.)

*Primary Examiner*—Alfred E. Smith
*Attorney, Agent, or Firm*—Clifton E. Clouse, Jr.; Roger S. Gaither; Michael F. Esposito

[57] ABSTRACT

In brief, the invention is a tomograph modified to be in a clamshell configuration so that the ring or rings may be moved to multiple sampling positions. The tomograph includes an array of detectors arranged in successive adjacent relative locations along a closed curve in a first position in a selected plane, and means for securing the detectors in the relative locations in a first sampling position. The securing means is movable in the plane in two sections and pivotable at one point and only one point to enable movement of at least one of the sections to a second sampling position out of the closed curve so that the ends of the section which are opposite the point are moved apart a predetermined space.

10 Claims, 8 Drawing Figures

PUBLICATIONS

Derenzo, "Detectors, Sampling, Shielding, and Electronics for Positron Emission Tomography", U.S. Dept. of Energy Technical Report No. LBL.13091, Lawrence Berkeley Lab., Univ. of Cal., 1981.

Budinger et al., "Transverse Section Reconstruction of Gamma-Ray Emitting Radionuclides in Patients", Reconstruction Tomography in Diagnostic Radiology and Nuclear Medicine, Univ. Park Press, Baltimore, 315–342, 1977.

Budinger, "A Primer on Reconstruction Algorithms", U.S. Dept. of Energy Technical Report No. LBL–8212, Lawrence Berkeley Lab., Univ. of Cal., 1978.

Derenzo et al., "Imaging Properties of a Positron Tomograph with 280 BGO Crystals", IEEE Trans. Nucl. Sci., vol. NS–28, No. 1, 81–89, 1981.

CLAMSHELL TOMOGRAPH

The U.S. Government has rights in this invention pursuant to Contract No. W-7405-ENG-48 between the U.S. Department of Energy and the University of California.

BACKGROUND OF THE INVENTION

The present invention relates to positron tomographs consisting of one or more detector rings, and more particularly it relates to obtaining high resolution in such a tomograph by sampling with the tomograph in a first position and then taking at least one other sample with the tomograph in another position in the same plane.

Rapid sequence imaging is an inherent advantageous characteristic of stationary positron tomographs wherein detection is accomplished by means of scintillation within crystals arranged in a ring around the subject to be examined. This rapid sequence imaging characteristic makes such instruments valuable diagnostic tools in the practice of medicine. However, because of insufficient linear sampling in stationary ring tomographs, the intrinsic resolution of the individual crystal detectors is not achieved. Resolution of these instruments therefore needs improvement. The greater the number of crystals, the better the resolution of the instrument. Therefore, a large number of crystal detectors are used in such instruments, along with complex electronic circuits for each detector.

In order to maximize the number of crystals in each ring and thereby enhance the resolution of the instrument, efforts have been made to closely pack the crystals. Such efforts are generally believed to have been carried to practical limits. Consequently, various other schemes have been suggested and tried to improve resolution. Notably, such schemes include sampling with the ring in a first position and then sampling at least one more time with the ring in a second position. There can also be additional positioning and sampling to further increase the resolution.

Various multiple positioning sampling schemes are described in the following references, all of which are incorporated herein by reference:

1. Phelps ME, Hoffman EJ, Mullani NA, et al: "Application of annihilation coincidence detection to transaxial reconstruction tomography", *J. Nucl. Med.* 16: 210–224, 1975.
2. Mullani NA, Ter-Pogossian MM, Higgins CS et al: "Engineering aspects of PETT V", *IEEE Trans. Nucl. Sci.*, NS-26: No. 2 2703–2706, 1979.
3. Ter-Pogossian MM, Mullani NA, Hood J, et al: "A multislice positron emission computed tomograph (PETT IV) yielding transverse and longitudinal images", *Radiology*, 128: 477–484, 1978.
4. Williams CW, Crabtree MC, and Burgiss SG: "Design and performance characteristics of a positron emission computed axial tomograph—ECAT-II", *IEEE Trans. Nucl. Sci.*, NS-26: No. 1, 619–627, 1979.
5. Bohm C. Eriksson L. Bergstrom M, et al: "A computer assisted ring detector positron camera system for reconstruction tomography of the brain", *IEEE Trans. Nucl. Sci.*, NS-25: No. 1, 624–637, 1978.
6. Brooks RA, Sank VJ, Talbert AJ, et al: "Sampling requirements and detector motion for positron emission tomography", *IEEE Trans. Nucl. Sci.*, NS-26: No. 2, 2760–2763, 1979.
7. Tanaka E. Nohara N, Yamamoto M, et al: "Positology - the search for suitable detector arrangements for a positron ECT with continuous rotation", *IEEE Trans. Nucl. Sci.*, NS-26: No. 2, 2728–2731, 1979.
8. Nohara N. Tanaka E, Tomitani T, et al: "Positologica: A positron ECT device with a continuously rotating detector ring", *IEEE Trans. Nucl. Sci.*, NS-27: No. 3, 1128–1136, 1980.
9. Cho ZH, Hong KS, Ra JB, et al: "A new sampling scheme for the ring positron camera-dichotomic ring sampling", *IEEE Trans. Nucl. Sci.*, NS-28: No. 1, 94–98, 1981.

In the foregoing references, various multiple positioning and sampling approaches to overcome the resolution limitation of stationary detector ring tomographs are described. These approaches include: scan-rotation motion of the ring, circular wobble, rotation of nonuniformly spaced detectors, and rotation of half-rings about the center.

In all of the foregoing approaches there are serious disadvantages. Each approach requires at least four and up to 100 positions to provide improved sampling at all angles with attendant mechanical and electrical complexity to achieve such motion accurately. Each approach also requires extensive electronic circuitry changes, and computer and computer programming changes to adapt a stationary, detector ring to the approach.

SUMMARY OF THE INVENTION

It is an object of the invention to improve the uniformity and resolution of tomographs by utilizing multiple sampling positions.

Another object is to improve the resolution of tomographs while minimizing the complexity of electrical and mechanical components, electronic circuitry, the associated computer and the computer programming.

Another object is to provide a simple, efficient, low cost tomograph of high resolution.

In brief, the invention is a tomograph modified to be in a clamshell configuration so that the ring or rings may be moved to multiple sampling positions. The tomograph includes an array of detectors arranged in successive adjacent relative locations along a closed curve in a first position in a selected plane, and means for securing the detectors in the relative locations in a first sampling position. The securing means is movable in the plane in two sections and pivotable at one point and only one point to enable movement of at least one of the sections to a second sampling position out of the closed curve so that the ends of the section which are opposite the point are moved apart a predetermined space.

Other objects and advantageous features of the invention will be apparent in a description of a specific embodiment thereof, given by way of example only, to enable one skilled in the art to readily practice the invention which is described hereinafter with reference to the accompanying drawing.

DESCRIPTION OF THE PRIOR ART

Figure 1A:
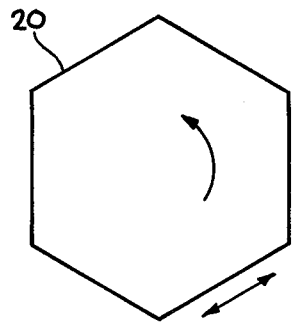
FIGS. 1a–1d are diagrammatic representations of various prior art schemes for improving the resolution of a ring tomograph.

Referring now to the drawing, there is shown in FIGS. 1a-1d schematic illustrations of various multiple positioning sampling schemes. In FIG. 1a is represented a hexagonal array of detectors 20 that is rotated through 60° under computer control, with coincident data from the detectors periodically recorded at typically 48 or more positions. This type of sampling scheme is described in more detail in references Nos. 1, 2, 3 and 4, itemized hereinbefore.

Figure 1B:
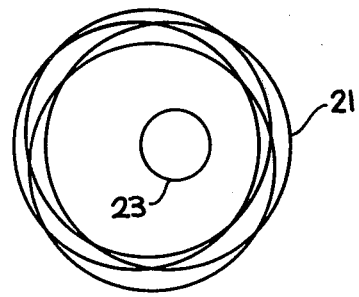

In FIG. 1b is represented a detector array 21 that is rotated eccentrically such as by an eccentric 23 so that each detector "wobbles" or rotates in a small circle near its original position. Coincident data is recorded for all detectors at predetermined corresponding points along the small circles. This type of sampling scheme is described in more detail in references Nos. 2, 5 and 6, itemized hereinbefore.

Figure 1C:
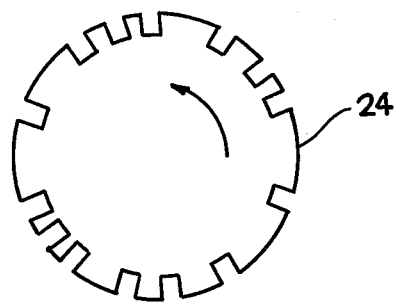

In FIG. 1c is represented a detector array 24 in which the detectors are nonuniformly spaced around the circumference of the array. Data is recorded in bins as the array is continuously rotated. This type of sampling scheme is described in more detail in references Nos. 7 and 8, itemized hereinbefore.

Figure 1D:
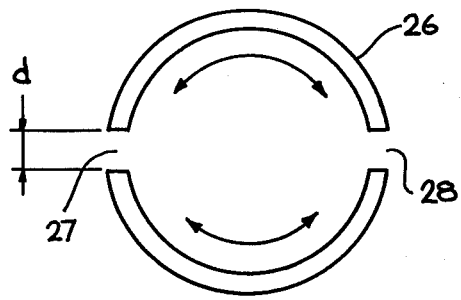

In FIG. 1d is represented a detector array 26 arranged around a circle but divided into two sections each less than one-half of the circle so that between the sections there are gaps 27 and 28 nominally equal to d, the width of an individual detector. The upper and lower sections may be moved along the circle so as to widen one gap and narrow the other. Coincident data are recorded in positions with one of the gaps typically at 0, d/2, d, 3d/2 and 2d. However, in all recording positions, all of the detectors lie along the circle about which the detectors are arranged. This type of sampling scheme is described in more detail in reference No. 9, itemized hereinbefore.

Reference will now be made in detail to a present preferred embodiment of the invention, an example of which is illustrated in the accompanying drawing. While the invention will be described in connection with a preferred embodiment, it will be understood that it is not intended to limit the invention to that embodiment. On the contrary, it is intended to cover all alternatives, modifications, and equivalents as may be included within the spirit and scope of the invention as defined in the appended claims.

DESCRIPTION OF THE PREFERRED EMBODIMENT

Figure 2:
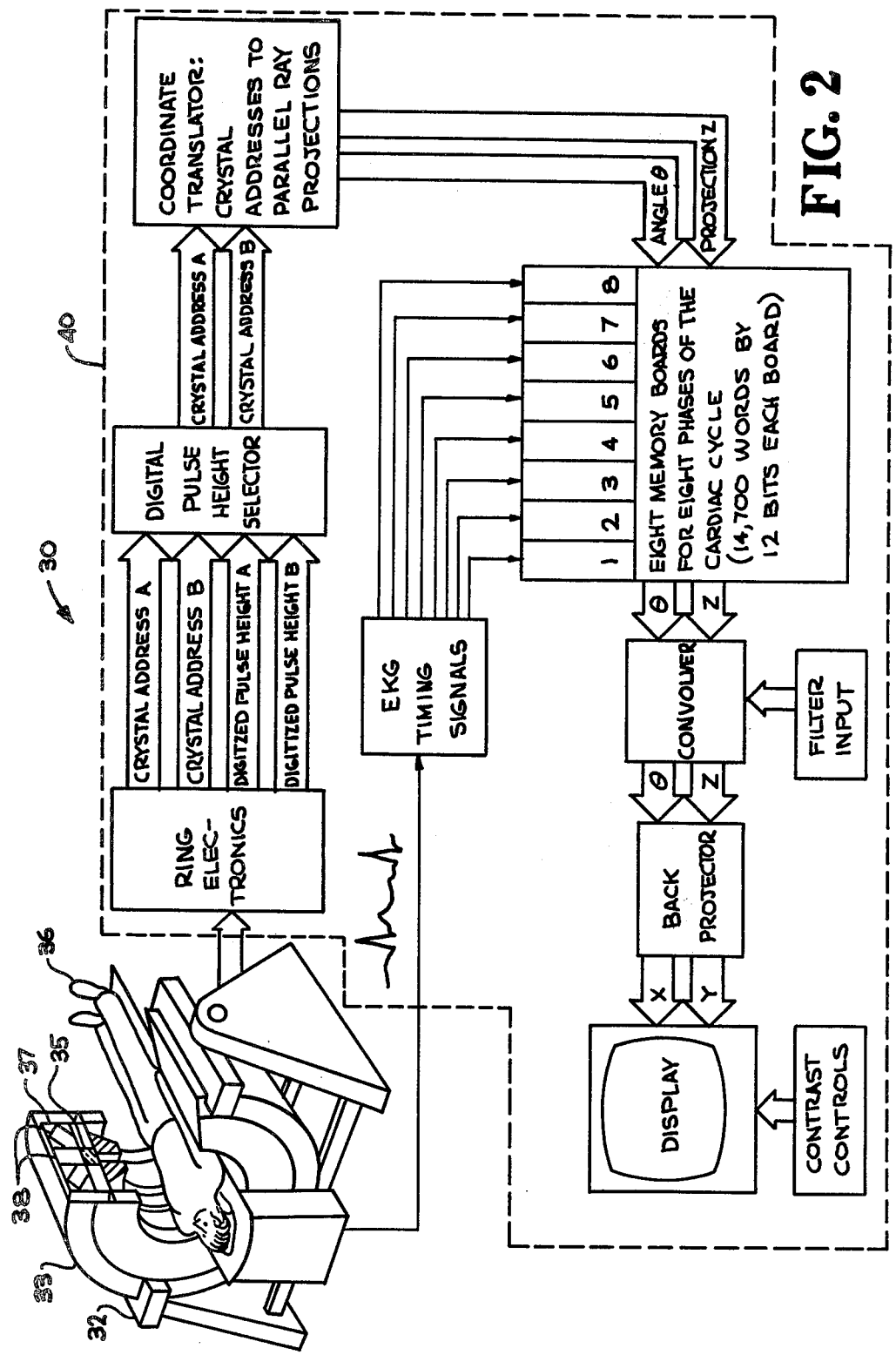
FIG. 2 is a perspective view of a tomograph system including a stationary ring detector, partially in cross section, and a block diagram of electronic circuitry for operating the system.

Referring to FIG. 2, a block diagram of a tomograph system 30 is shown that is suitable for incorporation of the invention therein. However, the invention is not limited to use in that system.

The system 30 represents the Donner Laboratory Positron Tomograph, Lawrence Berkeley Laboratory, University of California. This system is disclosed and described in detail in the following additional references which are incorporated herein by reference:

10. Derenzo SE, Budinger TF, Cahoon JL, Huesman RH, and Jackson HG, "High resolution computed tomography of positron emitters", IEEE Trans. Nucl. Sci., NS-24, No. 1, 544–558, 1977;
11. Derenzo SE, Banchero PG, Cahoon JL, Huesman RH, Vuletich T, and Budinger TF, "Design and construction of the Donner 280-crystal positron ring for dynamic transverse section emission imaging", Proceedings of the IEEE Conference on Decision and Control, IEEE 77CH1269-OCS, Vol. 1, 1977;
12. Derenzo SE, Budinger TF, Cahoon JL, Greenberg WL, Huesman RH, and Vuletich T, "The Donner 280-crystal high resolution positron tomograph", IEEE Trans. Nucl. Sci., NS-26, No. 2, 2790–2793, 1979; and
13. Huesman RH and Cahoon JL, "Data acquisition, reconstruction and display for the Donner 280-crystal positron tomograph", IEEE Trans. Nucl. Sci., NS-27, No. 1, 474–478, 1980.

In brief, the system 30 includes a gantry 32 for supporting a holding ring 33 shown with nearly a quarter section broken away in order to illustrate a plurality of crystal detectors 35 secured by a support 37 in a side-by-side arrangement around the inner circumference of the ring 33 so that one edge of each detector is exposed toward the central axis of the ring. An object or patient 36 to be examined is positioned along the central axis of the ring 33, with the portion of the subject to be specifically examined positioned opposite the detectors 35.

In the examination procedure, the patient is given a substance which will concentrate in the organ to be examined. The substance will contain positron emitting nucleis. The emitted positron will find and annihilate with an electron and emit two oppositely directed annihilation photons. These opposing photons are picked up by a pair of opposing crystal detectors which thereby scintillate in time coincidence. A photomultiplier 38 is mounted adjacent each crystal for transducing the scintillations to electrical pulses which are then applied to an electronics and display section 40 for processing and display on a video display unit 41 of a cross-sectional view of the organ being examined. The functions and operations of the section 40 are indicated generally in FIG. 2 and are more completely disclosed in the references 10–13 cited hereinbefore and incorporated herein by reference and will not be further discussed.

Figure 3:
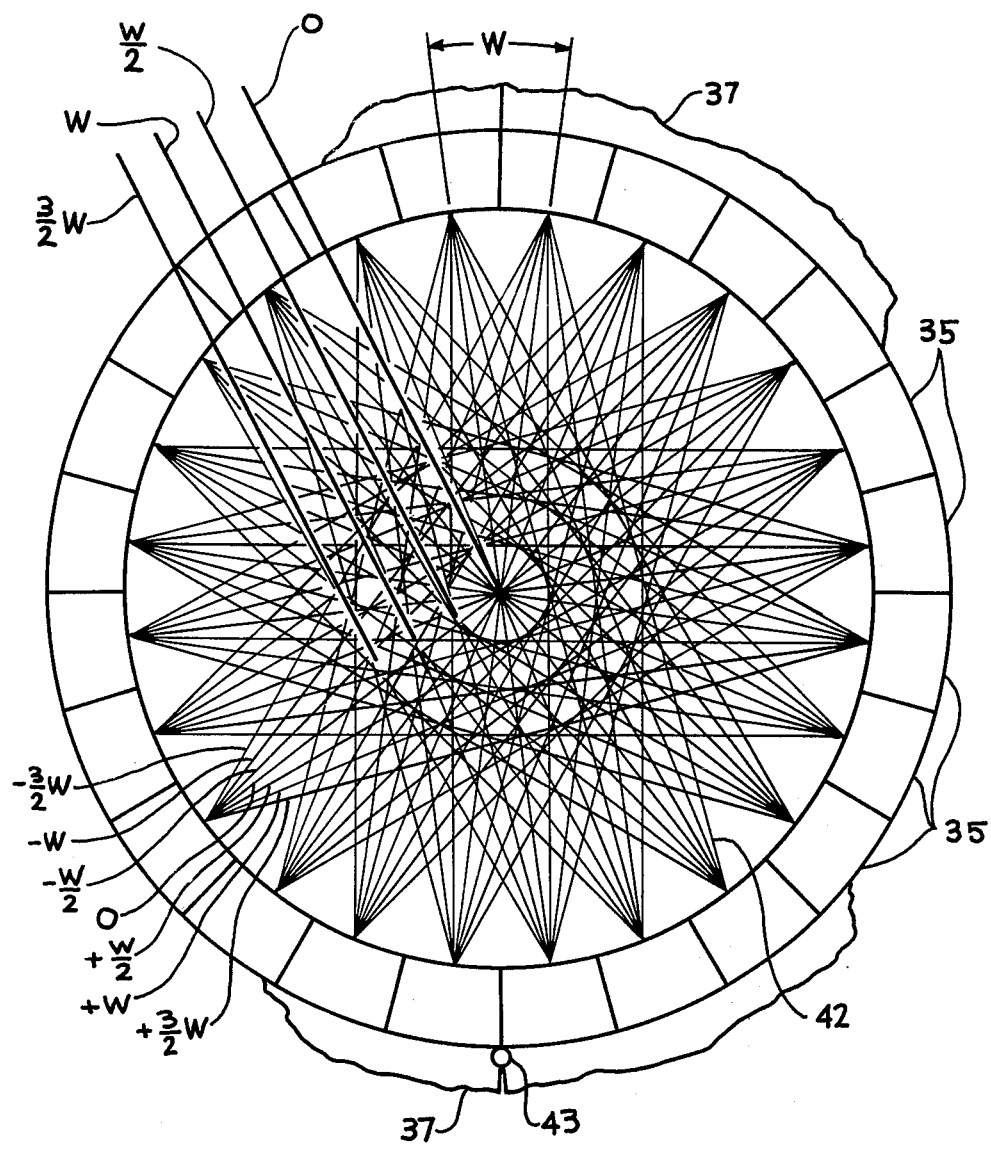
FIG. 3 is a diagrammatic representation of crystal detectors of the tomograph of FIG. 2 in a first sampling position with chords drawn between detectors that have been selected to be paired for sampling coincident radiation.

Referring to FIG. 3, the detectors 35 are shown in their normal circular arrangement for serially taking and processing data of pairs of annihilation photons successively presented during the examination procedure. In a typical positron tomograph, such as the Donner 280-BGO-Crystal Tomograph at the University of California, a circular arrangement of 280 crystals is used. However, for ease of illustration and explanation, only 24 crystals are shown in FIG. 3. Each of the crystals 35 is chosen to be paired with seven opposing crystals. The center-to-center spacing of the crystals is indicated as "w".

As mentioned hereinbefore, the positron emitting nucleus results in oppositely directed pairs of annihilation photons going in essentially opposite directions. These annihilation pairs occurring between paired crystals are represented by chords 42. The longest chords are between crystals positioned 180° apart, and they converge at the center of the circular arrangement of crystals. This center point is indicated as "0" at the end of a line drawn from the center. The chords between crystals that are less than 180° apart are shorter and converge to form a series of concentric "sampling rings". The radii of these rings are indicated at the ends of heavy lines drawn tangentially outward from the outer edges of successively larger rings from 0. These radii are labeled w/2, w, and 3/2 w. For any crystal 35, the chords may be labeled 0, ±w/2, ±w, and ±3/2 w to form the corresponding rings with radii 0, w/2, w, and 3/2 w. The number and relative closeness of such sampling rings is a measure of the resolution of a tomograph. In the present invention, the position of the crystals 35 in FIG. 3 constitute a first sampling position.

Figure 4:
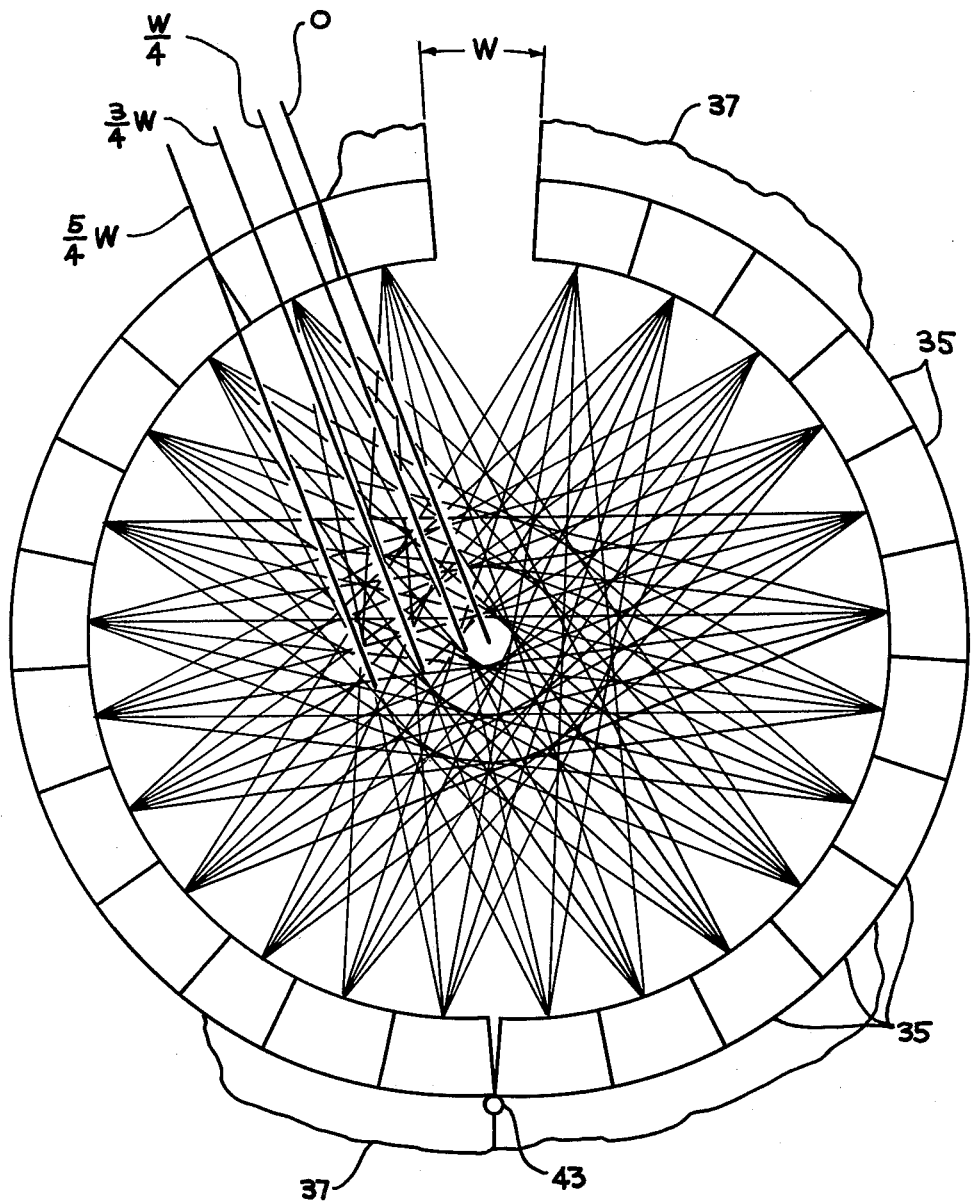
FIG. 4 shows the crystal detectors of FIG. 3 in a second sampling position, with a second set of chords drawn between detectors that have been selected to be paired, according to the invention.

In accordance with the invention, the number of sampling rings may be increased by moving the crystals 35 to a second sampling position by hinging the support 37, such as by a hinge 43, so that one-half of the crystals may be pivoted as a semicircular unit away from the other half for a distance of one crystal width w. The second sampling position of the crystals 35 is shown in FIG. 4.

In the second sampling position, the angle of opposing crystals is slightly reduced. However, for a tomograph having a very large number of crystals, this reduction is not significant.

Figure 5:
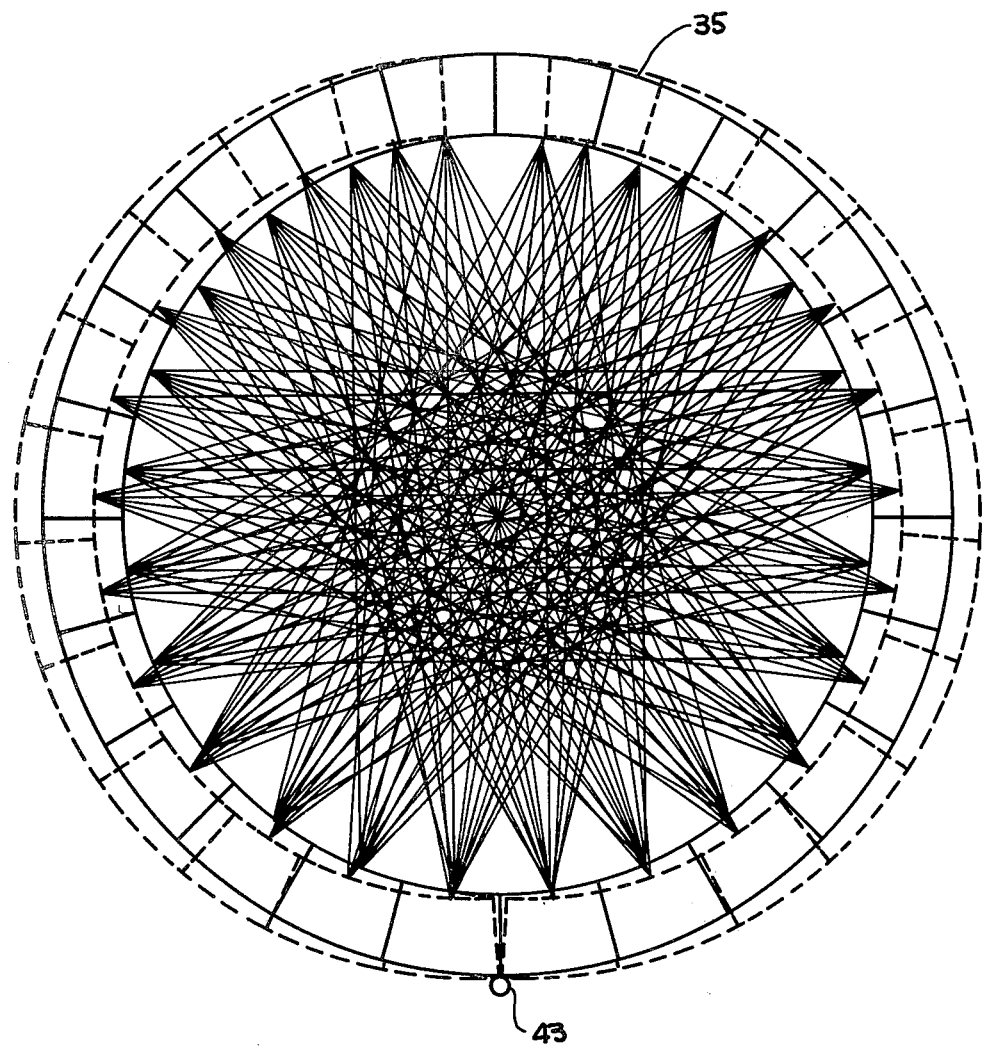
FIG. 5 shows the crystal detectors of FIG. 3 in the first sampling position, with the detectors in the second sampling position of FIG. 4 superimposed thereover with all of the chords that are also shown in FIGS. 3 and 4.

In the second sampling position, sampling rings with radii of w/4, 3/4 w, and 5/4 w are formed by chords between opposing crystals. The increased resolution of the system 30 by utilizing this second sampling position is graphically illustrated in FIG. 5 by superimposing the sampling rings of the first sampling position of FIG. 3 over those of the second sampling position shown in FIG. 4. No attempt has been made to label the rings in FIG. 5 since the rings are so closely spaced, and there is a multitude of interfering chords. However, it will be observed from the previous discussions that with two sampling positions, sampling rings are formed at 0, w/4, w/2, 3/4 w, w, 5/4 w, and 3/2 w. Thus, the linear sampling of the system 30 is improved over single position sampling by a factor of 2 at all angles taken around the holding ring 33 with only two mechanical positions of the cyrstals 35.

In operation of the system 30 according to the invention, a data set is obtained for each of the two sampling positions for processing in the section 40 (FIG. 2). The two data sets can be individually filtered by standard fan-beam reconstruction techniques such as set forth in the following, which is incorporated herein by reference:

14. Herman and Lung, "Reconstruction From Divergent Beans: A Comparison of Algorithms With and Without Rebinning", *Computers In Biology and Medicine*, Vol. 10, pp. 131-139, 1980.

The two data sets can then be added together during a backprojection. The resulting image has significantly less artifacts than the reconstruction of the individual data sets, but the resolution at full-width and half-maximum is only improved slightly when normal data bins are utilized that have a width of d/2 in both cases. To reconstruct the data sets with better resolution, a bin width of d/4 is used along with a parallel-ray reconstruction that differs in two ways from the standard method.

First, each data set is organized into sets of parallel projections of bin width d/4 where three out of every four bins are zero. These projections are filtered in the normal manner.

Second, the filtered projections are backprojected using a trapezoidal function whose flat top varies in width from zero at the center of the detector ring (i.e. triangular) to the full width of the crystal at the crystal faces (i.e. rectangular), and linearly between those extreme points. Each filtered data bin is backprojected along the same angle and position in the image space as the chord 42 between the corresponding detectors 35 was in the object space. The final image has high resolution and is the sum of the two backprojections, one from each data set.

While examples of preferred embodiments of the invention have been shown and described, further examples of the invention will be apparent to those skilled in the art without departing from the spirit of the invention. For example, the pivoting of the two crystal detector array halves a distance equal to one crystal width is for convenience and simplicity of calculation and adaptation to an existing system. However, it is envisioned that the two halves could be pivoted either an integral number of crystal widths or a fractional number of widths. It is further envisioned that instead of pivoting the crystal arrangement in halves, they could be pivoted in unequal sections, and that the number of crystals may be either even or odd. In addition, the application of this method could be for other sensing devices wherein senders and receivers are in a closed circle or a point sender is coupled to a full or part circle of receivers or vice-versa. The devices include sensors of electromagnetic radiation, particle radiation and sound.

What is claimed is:

1. In a tomograph system, the combination of:
   an array of detectors arranged in successive adjacent relative locations along a closed curve in a first sampling position in a selected plane; and
   means for securing said detectors in said relative locations in said first sampling position, said means being movable in said plane in first and second sections, said sections each having first and second ends, said means being pivotable at least at one of said first ends at one point and only one point to enable movement of at least one of said sections to a second sampling position out of said closed curve so that said second ends of said sections which are opposite said point are moved apart a predetermined space.

2. The combination of claim 1, wherein said sections are equal halves.

3. The combination of claim 1, wherein said tomograph system is a positron emission system and said detectors are crystal detectors.

4. The combination of claim 1, wherein said closed curve is circular.

5. The combination of claim 1, wherein said detector array has a width with an inner edge and an outer edge so that the inner edge of said array lies along an inner curve and the outer edge lies along an outer curve that is concentric with said inner curve, and wherein said means is pivotable at a point along said outer curve.

6. The combination of claim 1, wherein said sections are moved apart a space equal to at least the width of one detector.

7. A method for improving the resolution of a tomograph system that includes an array of detectors arranged in successive adjacent relative locations along a closed curve in a first sampling position in a selected plane, comprising the steps of:

pivoting a section of said array at one point and only one point out of said closed curve and away from a remaining section of said array so that said array is in a second sampling position with the ends of the said sections opposite said point moved apart a predetermined space.

8. The method of claim 7, wherein said system is a positron emission system, said detectors are cystal detectors and said sections are moved apart a space equal to at least the width of one crystal detector.

9. The method of claim 7, wherein said sections are equal halves.

10. The method of claim 7, wherein the number of detectors in each section is an even number.

* * * * *